(12) United States Patent
Schultz, Jr.

(10) Patent No.: US 6,360,619 B1
(45) Date of Patent: Mar. 26, 2002

(54) AVIATION FUEL SAMPLING SAFETY VALVE ASSEMBLIES

(76) Inventor: Robert L. Schultz, Jr., 520 3$^{rd}$ Ave., Avon by the Sea, NJ (US) 07717

( * ) Notice: Subject to any disclaimer, the term of this patent is extended or adjusted under 35 U.S.C. 154(b) by 0 days.

(21) Appl. No.: 09/379,812

(22) Filed: Aug. 23, 1999

(51) Int. Cl.$^7$ .................................................. G01N 1/00
(52) U.S. Cl. ...................................... 73/863.86; 137/613
(58) Field of Search ........................ 73/863.25, 863.86; 137/614.06, 614.2, 613; 251/149.9

(56) References Cited

U.S. PATENT DOCUMENTS

| | | | |
|---|---|---|---|
| 4,016,910 A | 4/1977 | Dumpis et al. | 141/226 |
| 4,020,834 A | 5/1977 | Bird | 128/145.6 |
| 4,036,257 A | 7/1977 | Hanson et al. | |
| 4,077,433 A | 3/1978 | Maldavs | 137/614.04 |
| 4,234,043 A | 11/1980 | Roberts | 166/336 |
| 4,580,453 A * | 4/1986 | Taylor | 73/863.86 |
| 4,598,581 A | 7/1986 | Brekke | 73/117.3 |
| 4,852,510 A | 8/1989 | Joseph, Jr. et al. | 116/140 |
| 4,930,664 A | 6/1990 | Ellison | 222/1 |
| 5,005,375 A | 4/1991 | Manz et al. | 62/292 |
| 5,074,332 A * | 12/1991 | Jones | 251/149.9 |
| 5,172,723 A * | 12/1992 | Sturgis | 137/613 |
| 5,269,030 A | 12/1993 | Pahno et al. | 5/604 |
| 5,320,133 A | 6/1994 | Nimberger | 137/614.04 |

FOREIGN PATENT DOCUMENTS

AU 209786 * 11/1955 ............ 137/641.06

* cited by examiner

Primary Examiner—Robert Raevis
(74) Attorney, Agent, or Firm—Christopher Whewell (57) ABSTRACT

The present invention provides a valve device by which samples of fluid materials may be removed from tanks, conduits, pipes, or sealed streams in which or through which they are caused to reside or travel. The device of this invention contains a reduced number of connections than devices of similar import in the prior art and further include an enhanced safety provision which prevents fluid leakage and inadvertent disconnection between the valve of this invention and a receptacle that is intended to receive the sample. The device of this invention is especially well-suited for use in routine sampling of the quality of aviation gasolines, turbine fuels, or the like at their point of use for contaminants detectable by a filtration method. However, a valve assembly according to this invention may be used in other applications requiring an accurate sample of material to be safely taken from containments which include inter alia, the aforementioned vessels.

16 Claims, 4 Drawing Sheets

AVIATION FUEL SAMPLING SAFETY VALVE ASSEMBLIES

This invention relates in general to valve assemblies, and in particular to valve assemblies useful in sampling liquid chemical streams in conduits during passage of a liquid stream through the conduit without an attendant interruption of the flow of the liquid. The assemblies of the invention are particularly well suited to assist in the sampling of reactive and/or hazardous liquid streams such as flammable liquids including gasolines. The valve assemblies of the invention are also anticipated as being useful in the sampling of gaseous streams in addition to liquid streams.

BACKGROUND

Since the first manufacture of chemical materials, perhaps by ancient Egyptians of the refining of gold, there has existed a need for a means by which the quality of the finished product to be used may be measured. In modern times, with the advent of the construction of chemical plants suitable to produce a wide range of reaction intermediates and finished products, both organic and inorganic, there has been seen an increased need for quality control measures. Such measures typically involve transporting a sample of a material to a laboratory or other facility for analysis, often on the same premises as the manufacture of chemical products themselves. The laboratory typically performs one or a plurality of chemical and/or physical analyses on the sample of material taken, with results being reported back to the workmen operating the chemical manufacturing process who then use the information gained to optimize or otherwise facilitate the production of materials.

Quite often, it is the case that the materials being sampled are hazardous or otherwise dangerous to personnel or the environment. In such instances extra care must be exercised to make certain that there are no releases of materials to the surroundings and that workmen in the manufacturing area are not exposed to even miniscule amounts of chemical streams involved. For example, as is known in the art, the manufacture of sulfurized olefins used in the transportation industry involves the reaction of molten sulfur under conditions of elevated temperature and pressure with hydrogen sulfide gas and an olefin such as butylene. During such a reaction, it is necessary to monitor the progression of the reaction, since the desirable product may consist in one having either two, three, four or more sulfur atoms per molecule. Since the reaction, if permitted to proceed unabated, would ultimately result in a sulfurized product containing more than the optimum desired amount of sulfur, a means by which the reaction mixture may be sampled without release into the atmosphere and without contacting a workman is necessary.

Another situation in which it is desirable to provide a means for sampling a chemical stream during the flow of a material through a conduit is in the sampling of aviation gasolines, turbine engine fuels, or the like, for contaminants at their point of use. The Federal Aviation Administration in the United States, and other analogous governmental agencies in countries foreign to the US have prescribed maximum levels of impurities permissible in various aviation fuels at their point of use. The determination of whether a particular fuel stream meets the required quality standards is typically carried out by performing an analytical test on the fuel stream near its point of use. During the carrying out of such test, it is necessary for an operator to extract a sample quantity of fuel from a conduit through which the fuel passes, desirably in such fashion that the workman is not exposed to the fuel and that none of the fuel is permitted to escape into the surroundings.

American Standard Test and Measurements ("ASTM") method ASTM D 2276, the entire contents of which are herein incorporated by reference, proscribes a standard test method by which particulate contaminants in aviation fuel by line sampling may be determined. The method involves the filtration of a known volume of fuel through a pre-weighed test membrane filter in a field monitor. During the filtration process, the membrane traps a mass of particulant contaminants, and the mass of the contaminants may be determined by a subsequent gravimetric analysis procedure. The official test method utilizes a field monitor to filter a sample of fuel that is taken in the field by the sampling method that is detailed in ASTM test method D5452, the entire contents of which are herein incorporated by reference thereto.

Typically, the filtration step involves the passage of a known volume of fuel through a Millipore™ type filtration membrane, which has a nominal pore size of approximately 0.8 microns. Therefore, it is desirable to have at hand a convenient means for controllably dispensing a specific sample quantity of fuel for filtration according to the standardized test method of determination of particulant contaminants. It is also desirable to have at hand a convenient means for extracting a sample of aviation fuel from a conduit through which it passes during normal use of the conduit, such as for example while it provides a source of fuel for commercial aircraft at busy airline hubs. It is thus seen to be highly desirable to provide for an uninterrupted flow of aviation fuels to their end users while also providing a means for extracting a sample for the above-described filtration test. The present invention provides a device especially well suited for such use.

The prior art provides devices for the sampling of fuel for the filtration test, and provides a means by which a representative sample of fuel may be removed from the conduit. For example, fuel sampling kits are available from Gammon Technical Products, Inc. of 2300 Highway 34, Manasquan, N.J., 08736, including those known as GTP-7; GTP-7T; GTP-3; GTE-5; and GTP-1, to name but a few. These kits are described in Fuel Sampling Equipment Bulletin 3 (12–95), available from Gammon Technical Products, Inc., the entire contents of which is incorporated herein by reference thereto. The kits typically include a main body portion (which includes a linear, tubular probe portion) that is adapted to be affixed to the external wall of a conduit in such fashion to permit the probe portion to extend to substantially the center of the conduit, so as to provide for the liquid removed to have come from the center of the conduit, thus providing a representative sample. The kits also include a quick-disconnect coupling that is equipped with a poppet valve, in addition to a ball valve. During use in extracting a fuel aliquot, the user connects the field filtration unit, which includes the Millipore™ type filter to the quick disconnect coupling. A ball valve is actuated by turning the handle, thus permitting fuel to flow until the valve is subsequently closed.

Assemblies produced from the aforementioned kits have the disadvantages in that they contain several joints, four (4) to be exact, between the various components of the sampling valves. Each such joint potentially serves as a point for leaks of fuel or otherwise the introduction of impurities into the system. Test procedure ASTM D-2276 specifies that the sampling valve connection "must have a minimum of internal recesses which could cause the holdup of contaminant".

Therefore, if a means for providing the removal of representative sample aliquots of chemical streams, including aviation fuels, while the overall flow of material to its end users could continue unabated and while reducing the number of potential leak points and having a unibody construction to reduce manufacturing costs, such a device would be welcomed by those personnel and companies who regularly engage in the evaluation of fuels, in addition to the environmental authorities interested in maintaining the cleanliness of the surroundings, as well as regulatory agencies such as OSHA and various labor organizations.

SUMMARY OF THE INVENTION

The present invention is directed at a valve device for providing representative samples of a fluid material from a conduit through which the fluid material is normally housed or caused to pass which comprises a substantially cylindrical valve body portion having a first end portion and a second end portion. There is a continuous hollow portion or "main bore" extending longitudinally through the valve body and parallel to its length dimension. The valve device also includes a valve means disposed between the first end portion and the second end portion effective for selectively separating the main bore into two separate chambers that are not in fluid contact with one another so as to prevent the flow of a fluid material through the main bore. The device further includes a means for causing said valve means to be in either an open or a closed position, which is preferably manually actuated, and a safety valve that is normally biased in a closed position disposed at the first end portion of the valve body. Preferably, the invention includes a tubular probe portion disposed at the second end portion of the valve body, in order to provide a user of the device a measure of control over the location at which the sample of fluid material is admitted for transmission through the valve of the invention to the filtration apparatus or other intended sample receiver.

The valve of the invention preferably includes a quick disconnect coupling pair, which include a male and female member. Preferably, the female member of a quick disconnect coupling is attached to the first end of the sampling device of the invention. There is also a safety valve (preferably a poppet-type valve) that is mechanically biased in a closed position to prevent the flow of fluid from a conduit through the valve in the event that the manually actuated valve is inadvertently caused to be in an open position, and in such regard, the poppet valve acts as a safety device. The safety valve is preferably located between the valve means and the female member of the quick disconnect pair and is preferably in a closed position during times when no filtration device is attached to the valve. This is readily accomplished through use of a biasing spring means which has a first end portion and a second end portion, wherein its first end portion is in mechanical contact with the moveable element of the poppet valve and the second end portion is in mechanical contact with a stationary spring seating means located at a suitable location within the main bore. The spring seating means is the valve packing in a preferred form of the invention.

The valve body means may include a boss portion, wherein the boss portion has a valve control bore through it that is adapted to receive the control shaft means that is used to actuate the valve means wherein the centerline of the valve control bore is substantially perpendicular to the centerline of the main bore. Typically, the means for manually causing the valve means to be in either an open or a closed position includes a control shaft portion having a first end portion and a second end portion wherein the first end portion is in mechanical contact with the valve means and wherein the second end portion includes a handle or other provision which enables the hand(s) of a workman to actuate the valve means from an open to a closed position.

One of the advantageous safety features of the device is its inclusion of a provision which prevents the disconnection of the mating portions of the quick disconnect coupling that has been engaged while the valve means disposed within the main bore is in the open position. Such a provision is capable of preventing inadvertent releases of fluid materials (which may be hazardous or inflammable) by workmen. This feature, coupled with the absence of the pluralities of linkages or couplings found in prior art devices of the type to which the instant invention pertains makes the instant device and the method of its use the premier method of choice for routine fuel quality sampling in the industry. Further, such safety is attainable at a price level which is cost competitive and readily affordable by the industry. Towards this end, advantageous use is made of the slidable outer collar portion coextensively disposed about the female portion of the quick disconnect coupling, and its cooperative connection with a provision on the handle means that prevents movement of said slidable outer collar portion of the safety (poppet) valve when the valve means is in an open position, thereby effectively preventing disconnection of the complementary counterparts of the quick disconnect coupling means at times when the valve means is in an open position.

DETAILED DESCRIPTION OF PREFERRED EMBODIMENTS

Figure 1:
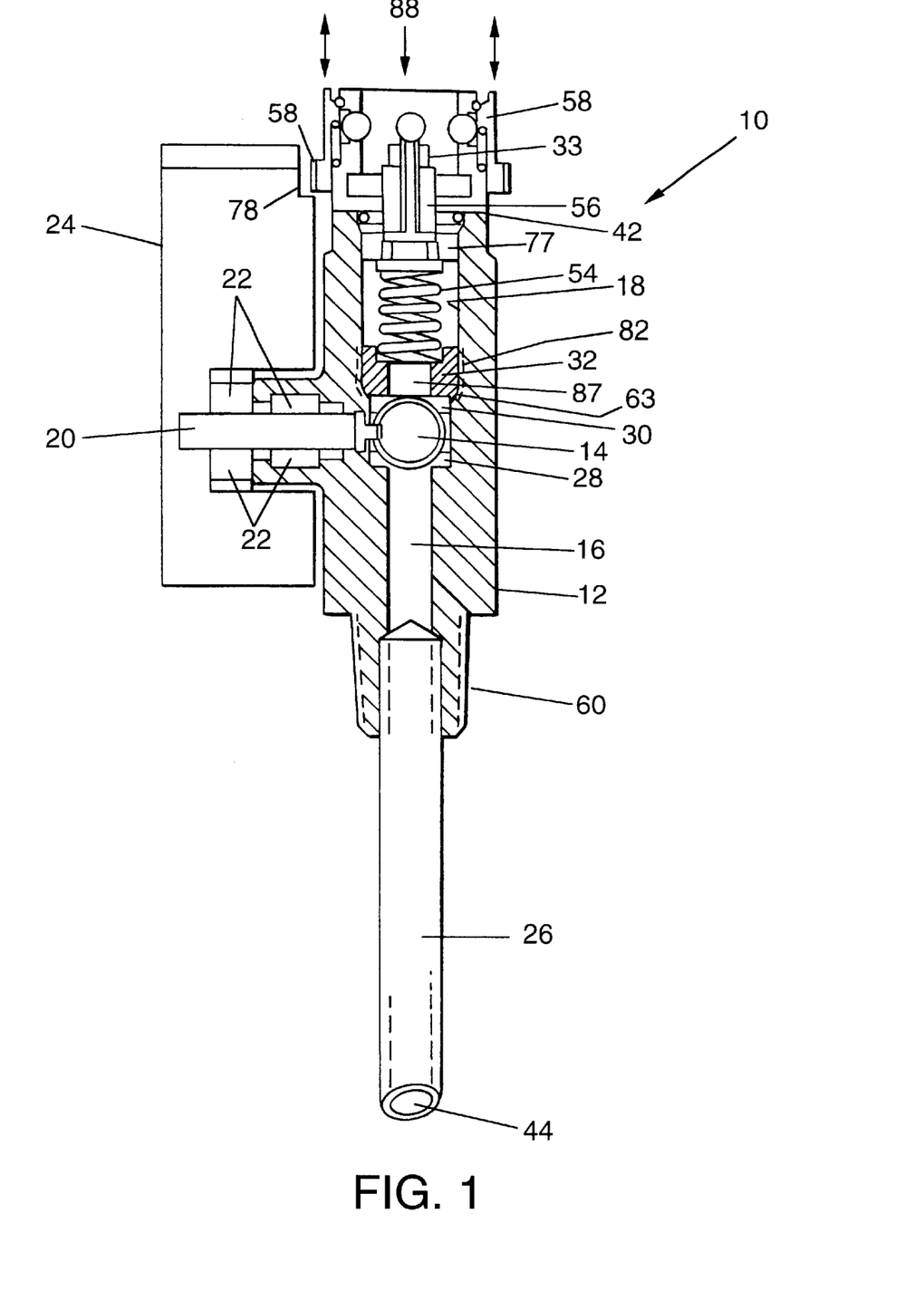
FIG. 1 is a cutaway side view of the device according to a preferred form of the invention.

Referring to the drawings and initially to FIG. 1 there is illustrated a sampling valve device 10 made in accordance with the principles of this invention. The sampling valve device 10 comprises a main valve body portion 12 having a first end portion 42 to which a quick-disconnect means 88 is attached and a second end portion to which an inlet probe 26 is preferably attached. The end portion to which the inlet probe 26 is attached is the end at which the fluid is to be withdrawn from its conduit or tank and is caused to enter the sampling valve 10 of the invention, hence this may be considered the inlet side of the sampling valve. The end portion 42 to which the quick-disconnect means 88 is attached is the end at which the fluid is to exit from the sampling valve of the invention, and this end may be considered the outlet side of the sampling valve of the invention.

There is a main bore that is preferably circular in cross section that extends through the main valve body portion from the inlet side of the device to the outlet side of the device, that preferably contains a minimum of recesses, including exposed threads. Located within the main bore portion is a valve means 14, which may be of any type of valve means known to those skilled in the art useful for controllably opening or closing a conduit to the flow of a fluid therethrough including gate valves, poppet valves, shuttle valves, plug valves, needle valves, elliptic valves, globe valves, iris valves, and "butterfly" valves. However, in a preferred form of the invention the valve means is a rotatable ball element, wherein the ball has a bore disposed through it through which the fluid passes. Accordingly, as used in this specification and the appended claims, the words "valve means" comprises all such devices provided by the prior art that are useful for controllably opening or closing a conduit to fluid flow through it, including without limitation ball valves. The valve means 14 is suitable for effectively and selectively isolating the portion of the main bore on the inlet side of the valve from fluid contact with the portion of the main bore on the outlet side of the valve. The diameter of the main bore may be uniform along the length of the valve body, but in the preferred form of the invention there are regions along the length of the valve body in which the main bore is of differing diameters. For example, the diameter of the bore 16 on the inlet side of the valve device of the invention near the inlet probe 26 in a preferred form of the invention corresponds approximately to the inner diameter of the probe portion, and is smaller in diameter than that portion of the main bore 18 located on the outlet side of the valve.

In mechanical contact with the valve means 14 is a shaft 20 which is useful for actuating the valve from an open position to a closed position by virtue of a torque applied through the shaft 20, preferably by an operator turning a handle means 24 which is in mechanical contact with the shaft 20. Shaft 20 is secured into a rotatable position by means of a sealing bushing 22 disposed about the shaft co-extensively, so that the bushing and shaft can be thought of as collectively comprising an assembly. Such sealing bushing or other means for sealing a control shaft for a valve against fluid leakage from the inside of the valve and the external surroundings are well known in the art, and any such known means are useful in connection with the instant invention. In a preferred form of the invention, the bushing is comprised of several washers stacked upon one another, which are held securely in place by virtue of the force applied by a nut that is disposed about threads on the external surface of the shaft. In yet another embodiment, the several washers are„held in position by the force of a screw which holds the handle means to the shaft. In such embodiments, the stack of washers act effectively as a bushing, providing support for the shaft while simultaneously sealing the interior of the valve means from the external surroundings. The bushing/shaft assembly is located within a boss portion 69 in which is disposed a second bore in the main valve body that is substantially perpendicular to the preferably round main bore portions 16 and 18.

As is common to most valve means, there are packing portions 28 and 30 disposed about the valve means. The packing portions have a twofold function of serving as a sealing surface about the valve means and the cavity in which the valve means and packing portions are located, as well as comprising a lubricative surface that promotes ease of actuation of the valve means. Preferably, the packing is constructed of an inert material having a low coefficient of friction, such as teflon®, or other materials known by those skilled in the art as being useful for valve packing in harsh chemical environments. In a preferred form of the invention, the round bore 18 on the outlet side of the valve means includes threads 82 on its inner surface which facilitate assembly of the device of the invention, including the secure positioning of the spring seat 32, as said spring seat is preferably shaped in the approximate form of a cylinder, and including a bore 87 completely through it about the centerline of the cylindrically-shaped spring seat to permit fluid flow through the device of the invention when the valve is in an open position and the moveable element 56 of the poppet valve is open. In accordance with the requirement set forth in ASTM testing procedure D-2276, it is preferable that the sampling valve connection "must have a minimum of internal recesses which could cause the holdup of contaminant". Therefore, the bore portion 18 preferably contains a minimal amount of threads necessary for the secure fastening of the spring seat 32 in its position against the valve packing 30, and just enough for one of the complementary counterparts of the quick disconnect coupling to be secured in place in an effectively sealed fashion. However, while it is preferable to minimize the total number of threads, the most important criteria is that there be no threaded portion exposed to the fuel as it flows through the valve. Therefore, it is most preferable that bore 18 is not threaded along its entire length, but contains threads only where the selected complementary counterpart of the quick disconnect engages the main valve body portion (at location 77) and where the spring seat 32 engages the main valve body portion (at location 63). Attached to the outlet end of the valve of the invention is one of the complementary counterparts of a quick-disconnect coupling means that is useful for connecting a tubing, conduit, or sample receiver that is intended to receive the fluid contained in the conduit to which the device 10 of this invention is in contact. The configuration and use of such quick disconnect coupling means is well known to those in the art, such as female portion (Model # MP 2883) and male portion (Model # MP 2468) available from Campbell Hausfeld Company, 100 Production Drive, Harrison, Ohio 45030, and typically used in pneumatic air hose connections involving compressed air and tools which are operated on compressed air, to cite but one example of these well-known couplings. Such quick disconnect coupling means include a female portion that is adapted to receive a male portion complementary thereto, and the female portion includes a plurality of metallic spheres disposed about the circumference of the wall located within its inner portion, in order to engage and lock into position the male portion of the quick disconnect coupling when such is inserted into the female portion.

The female portion of the quick disconnect coupling used in a preferred form of the invention includes a moveable outer sleeve portion 58 which is capable of moving in the direction of the arrows in FIG. 1, and the outer sleeve is mechanically biased in a direction away from the poppet valve. Therefore, when a complementary male portion is inserted into the female member to the quick disconnect coupling, it becomes locked in position by virtue of the spheres being caused to be pushed towards the center of the hole located within the female member, and thus engaging a ridge disposed coextensively about the circumference of the male member. Disengagement of the male member from the female member requires one to apply a linear force to the outer sleeve portion 58 in a direction towards the valve means 14, which releases the force on the spheres and permits the male member to be readily extracted from the female member, all of this being known to those skilled in the art of these common quick-disconnect couplings. Preferably, as shown in FIG. 1, it is the female portion of the quick disconnect coupling pair that is attached to the end of the main bore portion on the outlet side of the valve device of this invention. The male and female members are thus considered to be "complementary counterparts" for purposes of this specification and the appended claims, since they cooperate together to form a coupling through which fluid may be passed when they are in mating contact with one another. The words "complementary counterpart" may refer to either the male or female member of a coupling pair, depending upon the context used. Although the invention in its preferred form includes a female portion of a coupling pair attached to the end portion 42 of the main valve body portion, the present invention also contemplates the attachment of a substantially male in nature complementary counterpart to end portion 42.

Located within the outlet portion of the main bore 18, there is included in the preferred form of the invention also a safety valve assembly which is preferably a poppet valve and includes a movable poppet valve element 56 having a sealing surface (such as an O-ring) co-extensively disposed about the movable poppet element 56, a mating valve seat for the sealing surface of the movable poppet to rest to effectively close the poppet valve assembly and prohibit fluid flow, and a means for mechanically biasing the movable member of the poppet valve in a closed position against the poppet valve seat, wherein the biasing means preferably includes a spring 54. There is also a seat 32 for the spring to securely rest, preferably under a slight compression. The moveable element of the poppet valve 56 includes a tip portion 33, that in the final assembled version of the invention is disposed centrally within the female member of the quick disconnect assembly (that is disposed on the outlet end of the device 10) such that the poppet valve is caused to be actuated into an open position upon insertion of the male member of the quick disconnect coupling into the female counterpart by virtue of the male portion pressing against the tip portion 33 of the movable poppet element 56.

While the present invention has been described in terms of including a "safety valve" disposed between the valve means 14 and a member of a fluid coupling means, wherein the safety valve has been described as being a "poppet valve" in a preferred form of the invention, other types of safety valves including those belonging to the classes already mentioned herein. Accordingly, as used in this specification and the appended claims, the words "safety valve" includes all such valves. It is most preferable, however, that the safety valve be a poppet valve that is caused to be actuated into an open position upon the union of both members of a fluid coupling means, wherein at least one of the members of such coupling means is attached to the outlet end 42 of the main valve body portion of the invention. However, other valves that are capable of being mechanically biased in a closed position and located in such position that renders them capable of being actuated into an open position upon the union of the members of a fluid coupling means are herein indicated as being useful according to the invention, including without limitation the aforesaid valve types.

While the present invention has been described in terms of including a "quick-disconnect" coupling pair of the type depicted in the figures and described in this specification, other coupling pairs are herein indicated as being useful functional elements for purposes of making and using this invention. Accordingly, the present invention contemplates the use of any pair of separable mating couplings useful as being capable of being attached to an end portion of a conduit designed for carrying fluid materials, which are known to those skilled in the art. The quick-disconnect coupling including a female portion which comprises a slidable outer sleeve portion is merely a preferred one for use in the invention when it is desired to provided the added safety feature of prohibiting the disconnection of the coupling pair while the valve is in an open position. Therefore, for purposes of the instant specification and the appended claims the words "fluid coupling means" means a pair of mating couplings useful as a portion of a conduit (such as part of a tubing or hose) designed for carrying fluid materials, and includes the quick-disconnect device described herein. For purposes of this specification and the appended claims, the words "member of a fluid coupling means" means either one of the two mating couplings which comprise the fluid coupling means.

In the preferred form of the invention, an added safety feature is present which prohibits the disconnection of the male member from the female member of the quick disconnect pair during times when the valve means is in the open position. This feature makes the use of the instant invention to be preferred over devices in the prior art directed at similar utility, since it eliminates many potential accidents from occurring. In the preferred form of the invention, it is the female member of the quick-disconnect coupling which is attached to the outlet portion 42 of the device of the invention. The handle means 24 is contoured to contain a shoulder notch 78 so that when the valve means is in an open position, it is not possible to move the otherwise slidable outer sleeve portion 58 to permit disengagement of a male member that is engaged with the female member of the quick disconnect pair. By such provision, separation of the complementary counterparts of the quick disconnect coupling is not possible during times when the valve means is in an open position.

Figure 2:
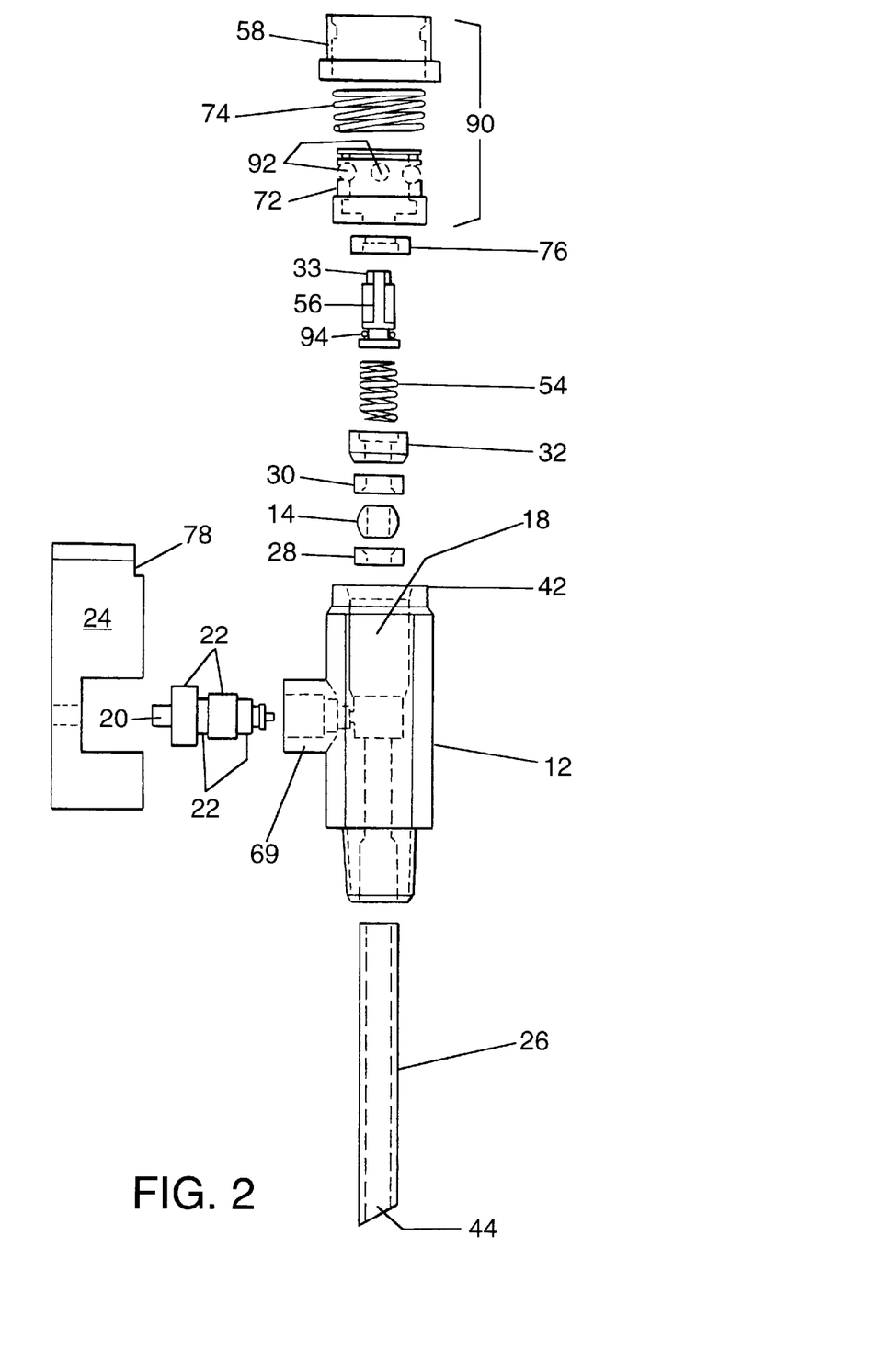
FIG. 2 is an exploded view of the various components of the device according to the invention in its preferred form.

FIG. 2 shows an exploded view of the various elements of the valve device of this invention and their respective positions according to a preferred form of the invention. In this figure, the main valve body portion 12 having boss 69 is depicted, showing probe element 26, shaft 20, bushing 22, and the handle means 24. Packing portions 28, and 30 valve means 14, and the spring seat 32 are shown, as well as spring means 54, and poppet valve movable element 56 having tip portion 33. The female member of the quick disconnect coupling pair 90, the construction of which is known to those skilled in the art, is shown to include a substantially cylindrically-shaped main body portion 72 having a plurality of retractable spherical elements 92 disposed about its inner wall portion, an outer sleeve portion 58, a spring means 74 for biasing the sleeve portion, and a linking portion 76 which preferably includes threads on its outer surface complementary to those disposed on the end portion of the bore on the outlet side of the main valve body 12. The linking portion of the female member of the quick disconnect coupling also includes a seat portion disposed coextensively about the bore disposed through the linking portion, that cooperatively mates with a corresponding sealing portion 94 on the poppet valve 56, which sealing portion is preferably an o-ring disposed about the outer surface of the poppet valve, as such a configuration is known to those skilled in the art.

Figures 3A, 3B:
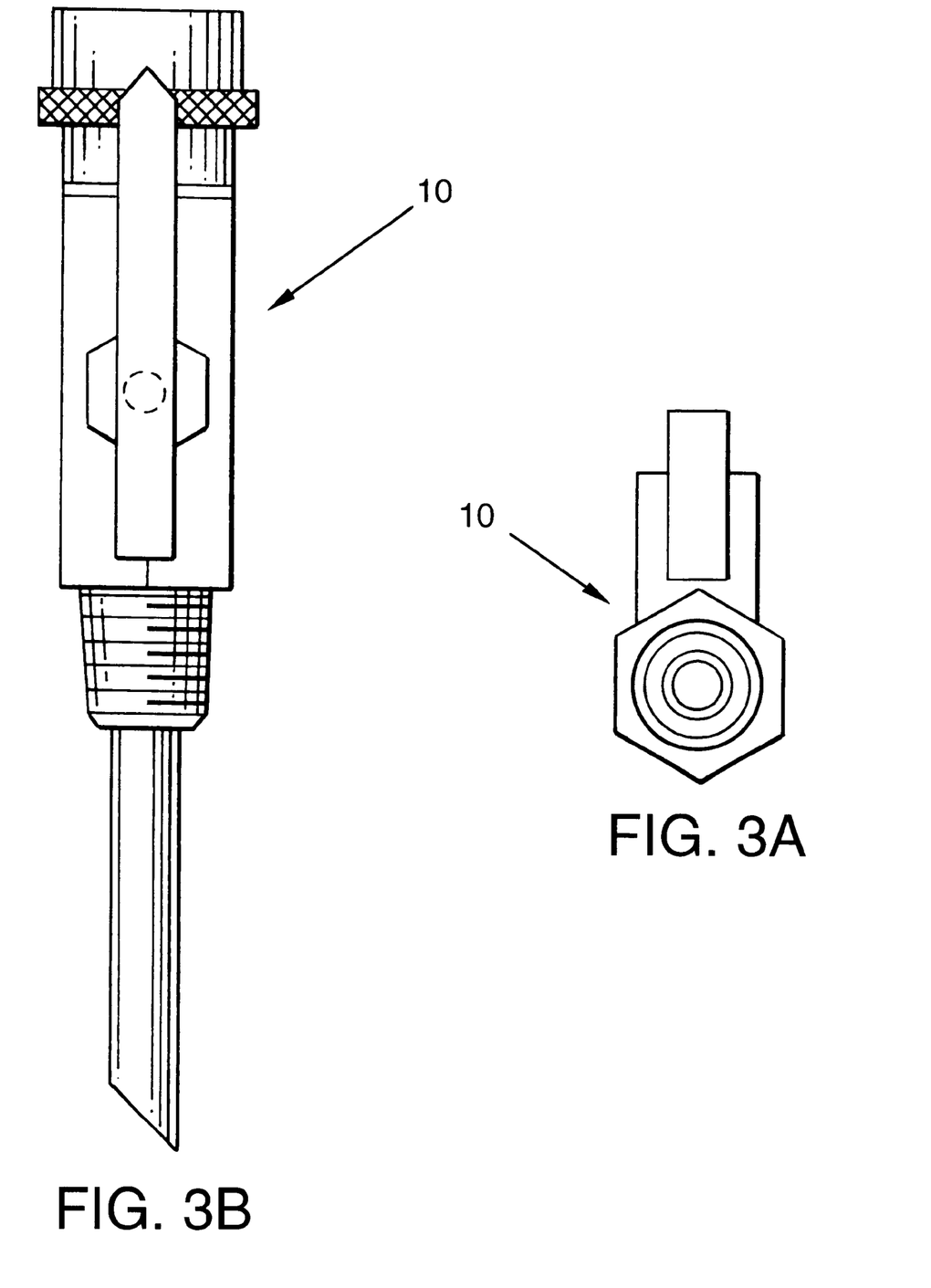
FIG. 3A is an end view of the device shown in FIG. 1.
FIG. 3B is a top view of the device shown in FIG. 1.

FIG. 3A depicts through an end view of the device of the invention the cross section of the device in a preferred form, which is hexagonal to permit ease of gripping with conventional tools for installation and removal purposes. FIG. 3B shows a top view of the device, conveying the geometry of the handle means in a preferred form of the invention and its location with respect to the other elements of the complete assembly.

Figure 4:
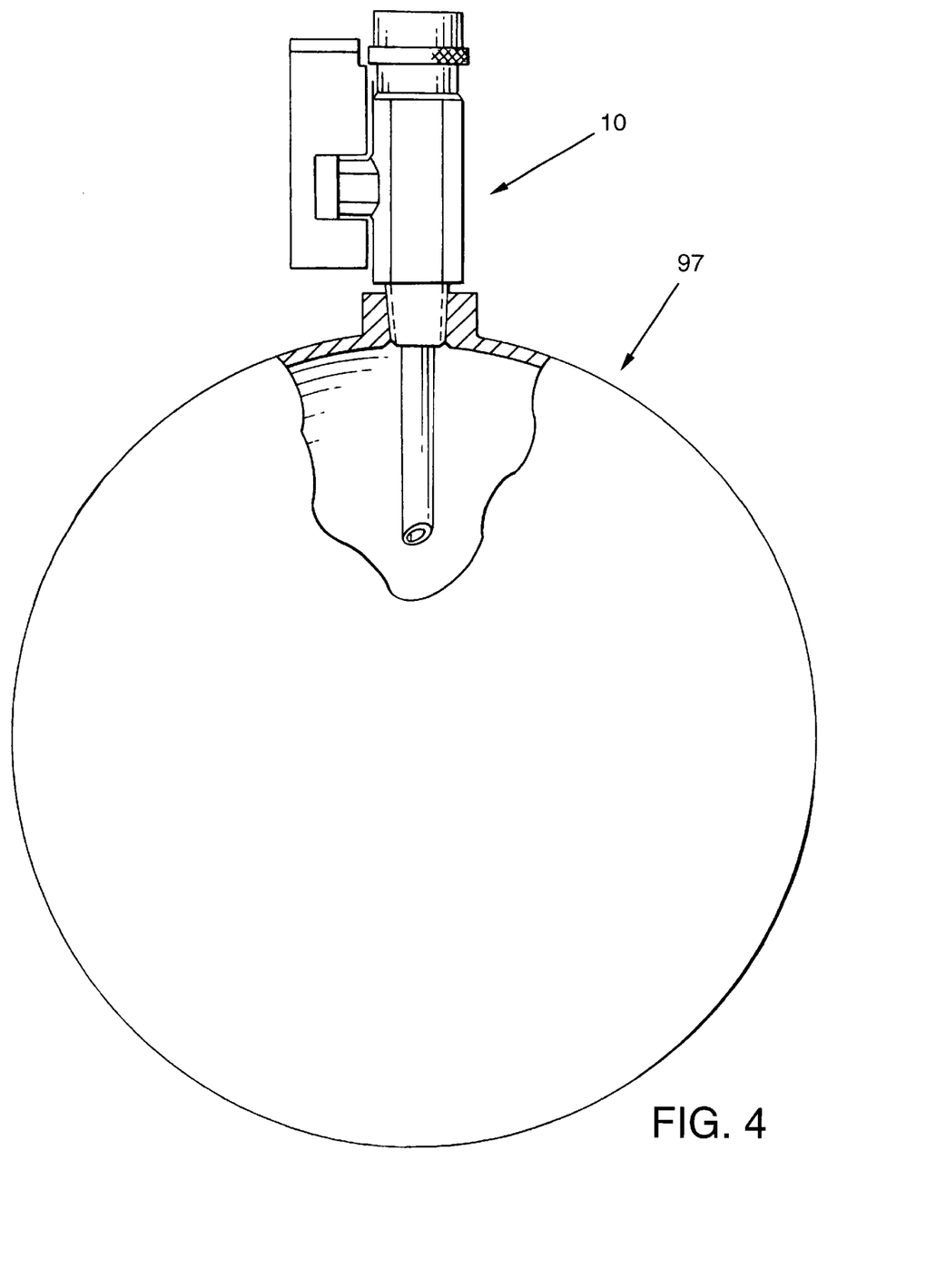
FIG. 4 shows a sectional view of a sampling valve device according to this invention installed in a conduit in which a fluid material is contained.

In FIG. 4 is shown a cross-section view of a sampling valve device according to this invention installed in a conduit 97 in which a fluid material is contained, showing the probe portion 26 disposed approximately in the center of such conduit to provide for a representative sample of material to be communicated to the outlet portion of the device of the invention.

To use the device of this invention, one provides a filtration field unit, sample container, or other vessel or system into which a sample of the fluid to be evaluated is to be transferred ("receiver"), said receiver having a male member of a quick disconnect coupling disposed at the portion of the receiver to which it is desired to admit the fluid that is to be evaluated, or at a hose, tubing, or other conduit attached to such location. The male member of the quick disconnect coupling is inserted into the female member in a locked, engaging fashion. Then, the receiver is prepared for the admission of the fluid to be inletted, and the valve means 14 is actuated to an open position thus permitting fluid to flow from the inlet end 44 of the probe 26 through the bore at the outlet side 18 of the valving means, through the quick disconnect coupling, and finally into the receiver. Fluid thereafter flows through the device 10 of the invention, until its flow is interrupted either by disconnection of the male member of the quick-disconnect coupling pair which causes the poppet valve to move to its closed position, or the actuation of the valve means to a closed position. In a preferred form of the invention, the valve means 14 must be closed in order for the members of the complementary counterparts of a quick-disconnect coupling means that is utilized to be separated from one another. In a preferred form of the invention, this means that the valve must be closed in order for a male member to be disengaged from its female counterpart, when a female portion of a quick-disconnect coupling is attached to the main valve body of a device according to the invention, as depicted in FIG. 1.

Poppet valves are well known in the art, and the use of a poppet valve in the instant invention is the preferred valve means useful for providing a fluid connection between the outlet side of the valve of this invention and the receiver. This is partially because it is desirable to have a quick and convenient means for connecting a receiver to a tank or conduit to be sampled. This is also because such an arrangement as herein described lends itself well to the added safety utility of the male member of a quick disconnect coupling means opening such a poppet valve merely upon its being inserted into the female member of the quick disconnect coupling pair. In addition, owing to the geometry of the elements of the invention, the female member of the quick disconnect also lends itself well to being effectively prohibited from releasing the male member of the quick disconnect pair when the handle means of the invention is in an open position. Examples of prior art showing poppet valves include U.S. Pat. Nos. 3,958,584; 3,999,430; 4,020,834; 4,063,708; 4,077,433; 4,103,712; 4,150,691; 4,321,384; 4,290,440; 4,363,424; 4,465,096; 4,549,675; and 4,566,489, the entire contents of which are herein incorporated by reference thereto. In order to be functional in the instant invention, such a poppet valve must include a movable poppet element having a sealing surface which is capable of mating in a sealing configuration with a complementary and cooperative stationary counterpart which serves as the valve seat. In the preferred form of the invention, the poppet valve seat is located within the linking portion 76 of the female portion of the quick disconnect pair. The valve seat is merely a surface upon which the sealing member of the poppet valve, for example, o-ring 94 may rest in the normally-closed position. Such a valve seat is reminiscent of the valve seat used in automotive cylinder heads for the past 40 years, and movable poppet valve elements and complementary seats thereto are well-known to those skilled in the art of fluid controls.

Although the handle portion of the invention in a preferred embodiment is shaped as shown in the various figures, other configurations are anticipated as being useful according to the principles of the invention, provided that adequate leverage is provided by a handle means for actuating the valve means between an open and a closed position. Such handle means could be a simple lever, as are known in the art of valve actuating handles. However, to be possessive of the added safety benefit utility as taught herein, a handle means needs to include a provision which permits part of its construction to effectively block the outer sleeve portion 58 of the female quick disconnect coupling pair from moving sufficiently to prohibit the removal of the male member of the quick disconnect coupling pair from the female portion when the valve is in an open position. Accordingly, any construction which contains an obstruction sufficient to block movement of the sleeve portion 58 when the valve is open is a functional equivalent to the discovery set forth herein. Such obstruction may include various configurations of tangs or other appendages affixed to the handle means.

The probe portion 26 of the invention functions to permit the user of the valve according to the invention to select the location within the conduit or other vessel from which it is desired to take a fluid sample. Preferably, the probe length is selected so that the portion of the probe that the fluid first enters is disposed at the approximate center of a conduit, when a conduit is the source of the fluid to be sampled. The probe is preferably attached to the main valve body portion by means of matching threads disposed about the outer portion of the probe and the inner portion of the bore on the inlet side 16 of the invention, although other functionally equivalent means are within the scope of the instant invention, including interference fits, welds, fasteners such as rivets, etc.

The main valve body portion 12 serves as the frame which either houses or to which the remaining elements are affixed. The main valve body, as well as the remaining components of the invention, may be comprised of various materials depending upon the intended application and conditions encountered. Included as suitable materials of construction are thermoplastic polymers, thermoset polymers, the various metal alloys known in the art to be useful for producing cast or forged tools, valve bodies and like wares, with stainless steel being the preferred material. The desired requisites are durability, cost-effective in manufacture, chemical resistance, and weight.

Although the valve assemblies of this invention have been described in relation to the filtration test for particulants contained in aviation fuel, it is anticipated that the valve assemblies according to the invention shall be found to have utility in the sampling of other liquid and even gaseous chemical streams. Therefore, the present invention is not limited in its application, owing to the mere selection of materials from which it is constructed, as the selection of suitable materials for use in a given application by a workman in a particular field of endeavor is well within the level of skill of the ordinarily skilled artisan.

Consideration must also be given to the fact that although this invention has been shown and described with respect to certain preferred embodiments, it is obvious that equivalent or functionally-equivalent alterations and modifications will occur to others skilled in the art upon the reading and understanding of this specification and the claims appended hereto. The present invention includes all such equivalent or functionally-equivalent alterations and modifications, and is limited only by the scope of the claims which now follow.

I claim:

1. A device for extracting a representative sample of a fluid material from a vessel or conduit in which said fluid material is contained or passes through which comprises:
   a) a substantially cylindrical main valve body portion which includes:
      vii) a first end portion;
      viii) a second end portion;
      ix) a main bore extending longitudinally through and parallel to the length dimension of said main valve body;
   b) a valve means disposed between said first end portion and said second end portion effective for selectively separating said main bore into two separate chambers that are not in fluid contact with one another;
   c) a means for manually causing said valve means to be in either an open or a closed position which includes a control shaft portion having a first end portion and a second end portion, wherein said first end portion is in mechanical contact with said valve means and wherein said second end portion includes a handle means;
   d) a member of a fluid coupling means disposed at said first end portion, said member including a slidable outer sleeve portion; and
   e) a safety valve disposed in said main bore and located between said valve means and said member of a fluid coupling means, wherein said safety valve is mechanically biased in a closed position,
wherein said handle means includes a shoulder notch, so that when the valve means is in an open position, it is not possible to move the slidable outer sleeve portion.

2. A device according to claim 1 wherein said safety valve is caused to be opened upon the coupling of said member of a fluid coupling means with its complementary counterpart.

3. A device according to claim 1 wherein said safety valve comprises a poppet valve.

4. A device according to claim 3 wherein said poppet valve is located in a position effective to permit said poppet valve to be opened upon coupling of said coupling member with its complementary counterpart.

5. A device according to claim 3 wherein said poppet valve is located in a position effective to permit said poppet valve to be opened upon coupling of said coupling member with its complementary counterpart by virtue of said complementary counterpart contacting and causing said poppet valve to open.

6. A device according to claim 3 in which said poppet valve is mechanically biased towards a closed position by virtue of a spring means in contact with said poppet valve.

7. A device according to claim 6 wherein said spring comprises a first end portion and a second end portion, wherein said first end portion is in mechanical contact with said poppet valve and said second end portion is in mechanical contact with a stationary spring seating means located within said main bore.

8. A device according to claim 7 wherein said spring seating means includes a passageway which permits the flow of a fluid therethrough.

9. A device according to claim 1 further comprising a tubular probe portion disposed at said second end portion.

10. A process for retrieving a fluid sample from a container or conduit which comprises the steps of:
    a) providing a device according to claim 9 wherein said probe portion is disposed within said container or conduit and in contact with a fluid;
    b) affixing a complementary counterpart to said member of a fluid coupling means;
    c) opening said valve means;
    d) collecting a sample of said fluid; and
    e) disconnecting said complementary counterpart from said member of a fluid coupling means.

11. A process according to claim 10 further comprising the step of closing the valve means prior to disconnecting said complementary counterpart from said member of a fluid coupling means.

12. A process according to claim 10 wherein said complementary counterpart is in fluid contact with a sample receiver.

13. A process according to claim 10 wherein said fluid is a hazardous substance.

14. A process according to claim 10 wherein said fluid is selected from the group consisting of: aviation gasolines and turbine fuels.

15. A device according to claim 1 wherein said member of a fluid coupling means is a female coupling.

16. A device for extracting a representative sample of a fluid material from a vessel or conduit in which said fluid material is contained or p asses through which comprises:
    a) a substantially cylindrical main valve body portion which includes:
       x) a first end portion;
       xi) a second end portion;
       xii) a main bore extending longitudinally through and parallel to the length dimension of said main valve body;
    b) a valve means disposed between said first end portion and said second end portion effective for selectively separating said main bore into two separate chambers that are not in fluid contact with one another;
    c) a means for manually causing said valve means to be in either an open or a closed position;
    d) a member of a fluid coupling means disposed at said first end portion; and
    e) a safety valve comprising a poppet valve disposed in said main bore and located between said valve means and said member of a fluid coupling means, wherein said poppet valve is mechanically biased towards a closed position by virtue of a spring means in contact with said poppet valve,
wherein said spring comprises a first end portion and a second end portion, wherein said first end portion is in mechanical contact with said poppet valve and said second end portion is in mechanical contact with a stationary spring seating means located within said main bore, and wherein said spring seat is the valve packing.

* * * * *